(12) United States Patent
Tass et al.

(10) Patent No.: US 7,974,698 B2
(45) Date of Patent: Jul. 5, 2011

(54) METHOD AND APPARATUS FOR DESYNCHRONIZATION OF NEURAL BRAIN ACTIVITY

(75) Inventors: Peter Tass, Titz (DE); Oleksandr Popovych, Düren (DE); Christian Hauptmann, Stolberg (DE)

(73) Assignee: Forschungszentrum Juelich GmbH, Juelich (DE)

( * ) Notice: Subject to any disclaimer, the term of this patent is extended or adjusted under 35 U.S.C. 154(b) by 245 days.

(21) Appl. No.: 11/441,251

(22) Filed: May 26, 2006

(65) Prior Publication Data

US 2006/0276853 A1    Dec. 7, 2006

Related U.S. Application Data

(63) Continuation of application No. PCT/DE2004/002336, filed on Oct. 20, 2004.

(30) Foreign Application Priority Data

Nov. 28, 2003  (DE) .................................. 103 55 652

(51) Int. Cl.
*A61N 1/36* (2006.01)
(52) U.S. Cl. ........................................................ 607/45
(58) Field of Classification Search ............... 607/45, 607/46, 62; 600/544, 545
See application file for complete search history.

(56) References Cited

U.S. PATENT DOCUMENTS

| | | | |
|---|---|---|---|
| 4,712,558 A * | 12/1987 | Kidd et al. ..................... | 607/48 |
| 6,366,813 B1 | 4/2002 | DiLorenzo | |
| 6,459,936 B2 * | 10/2002 | Fischell et al. .................. | 607/45 |
| 6,480,743 B1 | 11/2002 | Kirkpatrick et al. | |
| 6,529,774 B1 | 3/2003 | Greene | |
| 6,944,501 B1 * | 9/2005 | Pless .............................. | 607/45 |
| 2002/0072770 A1 * | 6/2002 | Pless .............................. | 607/2 |
| 2002/0077670 A1 * | 6/2002 | Archer et al. .................. | 607/45 |

FOREIGN PATENT DOCUMENTS

| | | |
|---|---|---|
| CA | 2479046 | 9/2003 |
| DE | 102 11 765 A1 | 10/2003 |
| DE | 102 11 766 B4 | 10/2003 |
| DE | 102 33 960 A1 | 2/2004 |
| DE | 103 18 071 A1 | 11/2004 |

(Continued)

OTHER PUBLICATIONS

Peter A. Tass, "Desynchronizing Double-pulse Phase Resetting and Application to Deep Brain Stimulation", Biological Cybernetics, Springer Verlag, Berlin, DE, Bd. 85, Nr. 5, Nov. 2001, XP002245895, pp. 343-354.

(Continued)

*Primary Examiner* — Carl H Layno
*Assistant Examiner* — Luther G Behringer

(57) ABSTRACT

The invention relates to an apparatus for desynchronization of neural illness-synchronous brain activity in which the activities in at least two subareas of a brain area or at least two functionally associated brain areas are stimulated by means of at least two electrodes. In the case of a person with an illness, desynchronization therapy suppresses symptoms in the relevant neuron population. The feedback stimulation signal, that is to say the measured, time-delayed and process neural activity, is used as an individual stimulus. This results in self-regulated, demand control of the amplitude of the stimulation signal, thus minimizing the intensity of the stimulation stimuli automatically after successful desynchronization. The apparatus has at least two stimulation electrodes and at least one sensor, which are driven by a controller such that they result in desynchronization in their local environment.

10 Claims, 5 Drawing Sheets

FOREIGN PATENT DOCUMENTS

| | | |
|---|---|---|
| EP | 1 405 652 A2 | 4/2004 |
| WO | WO 03/077985 A1 | 9/2003 |
| WO | 2004/016165 A1 | 2/2004 |
| WO | WO 2005/053787 A1 | 6/2005 |

OTHER PUBLICATIONS

P. A. Tass, "Desynchronizing Double-pulse Phase Resetting and Application to Deep Brain Stimulation" Biological Cybernetics 85, pp. 343-354 (2001).

English Translation of the Japanese Office Action mailed on Jun. 16, 2009 and issued in corresponding Japanese Patent Application 2006-540150.

Office Action mailed Oct. 22, 2009 is related U.S. Appl. No. 11/604,284.

Office Action mailed Aug. 5, 2009 is related U.S. Appl. No. 11/604,284.

International Search Report (Form PCT/ISA/210) of International Application No. PCT/DE2005/000780, Date of Mailing of the International Search Report: Sep. 5, 2005, in an application related to U.S. Appl. No. 11/604,284.

Taas, Peter A., et al., "Obsessive Compulsive Disorder: Development of Demand-Controlled Deep Brain Stimulation with Methods from Stochastic Phase Resetting", Neuropsychopharmacology, 2003.

Office Action mailed on Apr. 20, 2010 in related U.S. Appl. No. 11/604,284.

U.S. Appl. No. 11/604,284, filed Nov. 27, 2006, Method and device for decoupling and/or desynchronizing neural brain activity, Forschungszentrum Juelich GMBH, Juelich, Germany.

\* cited by examiner (A)

(B)

METHOD AND APPARATUS FOR DESYNCHRONIZATION OF NEURAL BRAIN ACTIVITY

This application is a continuation under 35 U.S.C. §111(a) of PCT International Application number PCT/DE2004/002336, and claims the benefit of PCT international application number PCT/DE2004/002336 filed Oct. 20, 2004 and German Application No. 103 35 652.4, filed Nov. 28, 2003, in Germany, the disclosures of which are incorporated herein by reference.

The invention relates to an apparatus for desynchronization of neural brain activity as claimed in the precharacterizing clause of claim 1.

BACKGROUND OF THE INVENTION

In the case of patients with neurological or psychiatric illnesses, for example Parkinson's disease, essential tremor, dystonia or compulsion disorders, nerve cell groups in defined areas of the brain, for example the thalamus and the basal ganglia are active because of the illness, for example being excessively synchronous. In this case, a large number of neurons form synchronous action potentials; the neurons involved fire excessively synchronously. In healthy persons, in contrast, the neurons fire qualitatively differently in these brain regions, for example in an uncorrelated manner.

In the case of Parkinson's disease, the pathologically synchronous activity, for example of the thalamus and of the basal ganglia, changes the neural activity in other brain regions, for example in areas of the cerebral cortex, such as the primary motor cortex. In this case, the pathologically synchronous activity in the area of the thalamus and of the basal ganglia forces itself, for example, on the rhythm of the cerebral cortex so that, in the end, the muscles which are controlled by these areas carry out a pathological activity, for example a rhythmic tremor.

In the case of patients who cannot (can no longer) be treated with medicaments, a deep electrode is implanted on one side or both sides depending on the clinical signs and depending on whether the illness occurs on one side or both sides. In this case, a cable leads under the skin from the head to the so-called generator, which comprises a controller with a battery and, for example, is implanted under the skin in the area of the clavicle. The deep electrodes are used to carry out a continuous stimulus with a high-frequency periodic sequence (pulse train at a frequency of >100 Hz) of individual pulses, for example square-wave pulses. The aim of this method is to suppress the firing of the neurons in the target regions. The effective mechanism on which the standard deep stimulation is based has not yet been adequately explained. The results of a number of studies indicate that standard deep stimulation acts in the same way as reversible lesion formation, that is to say in the same way as reversible deactivation of the tissue: standard deep stimulation suppresses the firing of the neurons in the target regions and/or in brain areas linked thereto.

This type of stimulation has the disadvantage that the power consumption of the generator is very high, so that the generator including the battery frequently has to be replaced operatively after only about one to three years. It is even more disadvantageous that the high-frequency continuous stimulation, as a non-physiological (unnatural) input in the area of the brain, for example of the thalamus or of the basal ganglia, can lead to adaptation of the relevant nerve cell groups over the course of a few years. In order to achieve the same stimulation success, a greater stimulus amplitude must then be used for stimulation, as a consequence of this adaptation. The greater the stimulus amplitude is, the greater is the probability that the stimulation of adjacent areas will lead to side-effects—such as dysarthria (speech disturbances), dysesthesia (in some cases highly painful false sensations), cerebellary ataxia (incapability to stand safely without an external aid), or symptoms similar to schizophrenia, etc. These side-effects cannot be tolerated by the patient. In these situations, the treatment thus loses its effectiveness after a few years.

In the case of other stimulation methods, such as those described in DE 102 11 766.7 A1, it has been proposed that stimuli be applied in the respective target region on a demand-controlled basis. The aim of these methods/these apparatuses is not simply to suppress the illness-synchronous firing—as in the case of standard deep stimulation—but to change this to be closer to the physiological, uncorrelated firing pattern. The aims of this are on the one hand to reduce the power consumption and on the other hand to use the demand-controlled stimulation to reduce the amount of energy introduced into the tissue in comparison to the standard deep stimulation.

SUMMARY OF INVENTION

The stimulation methods mentioned above use individual pulses, high-frequency pulse trains and low-frequency pulse trains as stimulation signals, which either suppress the dedicated dynamics of the stimulated neurons or change the neuron population to be desynchronized to an N-cluster state by means of a phase reset. The stimulation pulse trains are constructed without using the dedicated dynamics of the neuron population to be desynchronized and, in this sense, are external and unphysiological signals for the neuron population to be desynchronized. In order to suppress the illness symptoms, the stimulation pulse trains would have to be applied with a high intensity, which leads to the expectation that the neuron population to be desynchronized would adapt itself to the unphysiological stimuli, and possible side-effects.

The subject matter of the invention is thus to provide an apparatus for desynchronization of neural brain activity, by means of which patients with illness-synchronized brain activity can be treated mildly and efficiently. One aim in this case is to suppress adaptation to an unphysiological continuous stimulus. Tedious calibration processes should be avoided, and the stimulation should also be successful even when the main-frequency component of the pathologically rhythmic activity is subject to major fluctuations. Furthermore, the apparatus is intended to achieve long-term desynchronization, while very largely avoiding transient, stimulation-dependent unphysiological states. The apparatus according to the invention does not require any additional demand controller, which may be added optionally as described in Section 6.3, so that it can be implemented easily and only minor demands are placed on the complexity of the control electronics, and thus on the power consumption as well. The stimulation apparatus according to the invention is intended to operate in a power-saving manner, so that the batteries of the stimulator which is implanted in the patient need not be operatively replaced as often.

Against the background of the precharacterizing clause of claim 1, the object is achieved according to the invention by means of the features specified in the characterizing part of claim 1. Using the measured and processed activity of the neuron population to be desynchronized as a feedback stimulation signal, see Section 3, the object is achieved of the neurons in at least two subareas of a brain area or at least two functionally associated brain areas each having their activity influenced by the use of at least two electrodes for stimulation with individual stimuli with different time delays, in such a way that this surprisingly results in complete desynchronization of the stimulated neuron population, thus suppressing the symptoms in a person with an illness. For this purpose, the apparatus according to the invention has a controller 4 which records the measurement signal from the sensor 3 or the sensors 3, generates at least two stimulation signals from this signal, and passes them to the electrodes 2.

The apparatus according to the invention operates in a power-saving manner, so that batteries that have been implanted in the patient may be replaced less-often.

The apparatus according to the invention makes it possible to use the effect, achieved intraoperatively by the desynchronizing stimulation, for selection of the most suitable target point for the deep electrode. For this purpose, a test stimulus is carried out in advance in millimetric steps using the apparatus according to the invention in the area of the target point as calculated anatomically in advance, during the implantation of the deep electrode. The target point at which the best therapeutic effect can be achieved is chosen as the target point for the long-term implantation. Furthermore, in addition to the illnesses which have been mentioned above and which frequently have long-lasting pathologically synchronous activity at a relatively constant frequency, illnesses can also be treated in which pathologically synchronous activity occurs only intermittently (occurring for a short time). One major indication in this case is the treatment of epileptics who cannot (can no longer) be treated with medicaments. For example, the apparatus according to the invention can be used to achieve desynchronization in the illnesses of Parkinson's disease, essential tremor, dystonia, epilepsy and compulsive disorders.

Advantageous developments of the invention are specified in the dependent claims.

BRIEF DESCRIPTION OF DRAWINGS

The figures show exemplary embodiments of the invention, in which.

DETAILED DESCRIPTION

Figure 2:
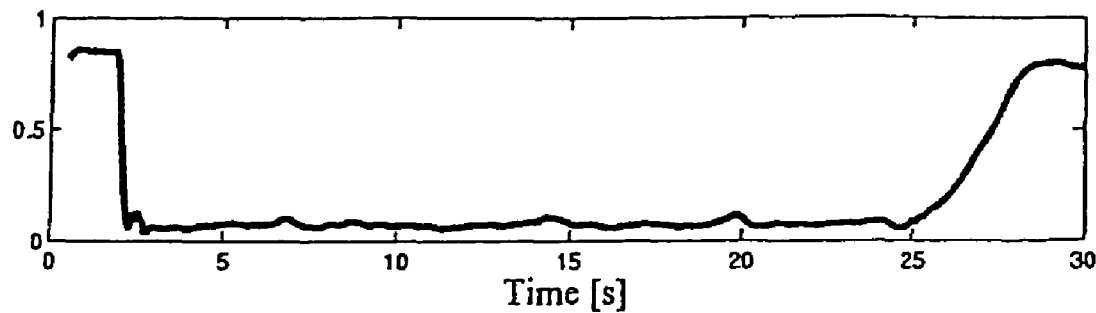
FIG. 2a: shows the waveform of the synchronization measure during one stimulation interval. Low (high) values correspond to low (high) synchronization. The stimulation starts at the time 2 seconds and is ended at the time 25 seconds.
FIG. 2b: shows the waveform of the neural activity of the nerve cells measured using the sensor 3 during the stimulation in FIG. 2.
FIG. 2c: shows the waveform of the individual stimulus applied via an electrode 2 during the stimulation in FIG. 2.
Figure 2:
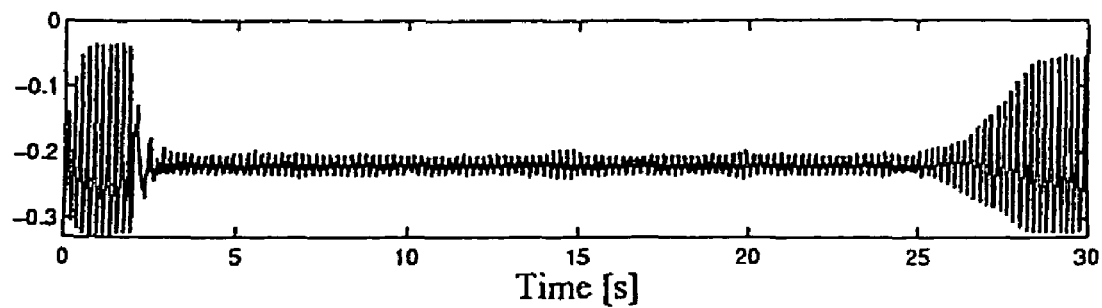
Figure 2:
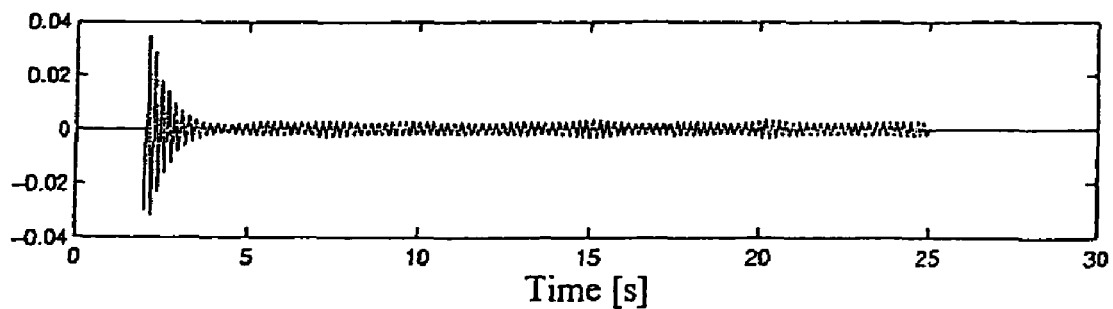

In FIGS. 2a, b and c, the abscissas denote the time axes in seconds, while the synchronization measure (FIG. 2a), the measured neural activity (FIG. 2b) and an example of a single stimulus (FIG. 2c) are plotted, in each case in arbitrary units, on the ordinates. The neural activity (FIG. 2b) measured by means of the sensor 3 is used as the basis for creation of the individual stimuli. The neural activity (FIG. 2b) measured using the sensor 3 is used as a control signal for the stimulus application.

Figure 3:
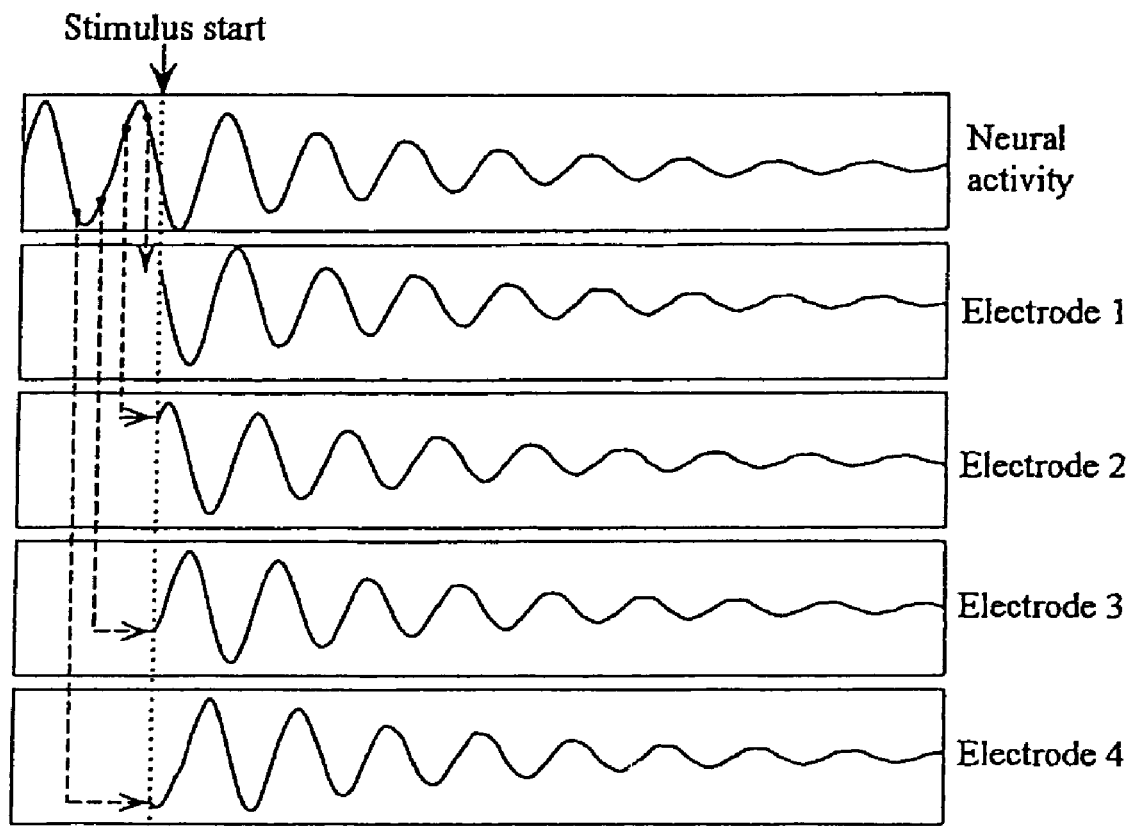
FIG. 3: shows an example of one application of a stimulation pattern via 4 electrodes with four different time delays.

In FIG. 3, the abscissa is the time axis in seconds, while the measured neural activity and the individual stimuli, for example in the sense of the applied current, are illustrated, in each case in arbitrary units, on the ordinate. The same stimulation pattern with the same polarity is applied via the four electrodes 2, but with four different, for example equidistant, time delays.

Figure 4:
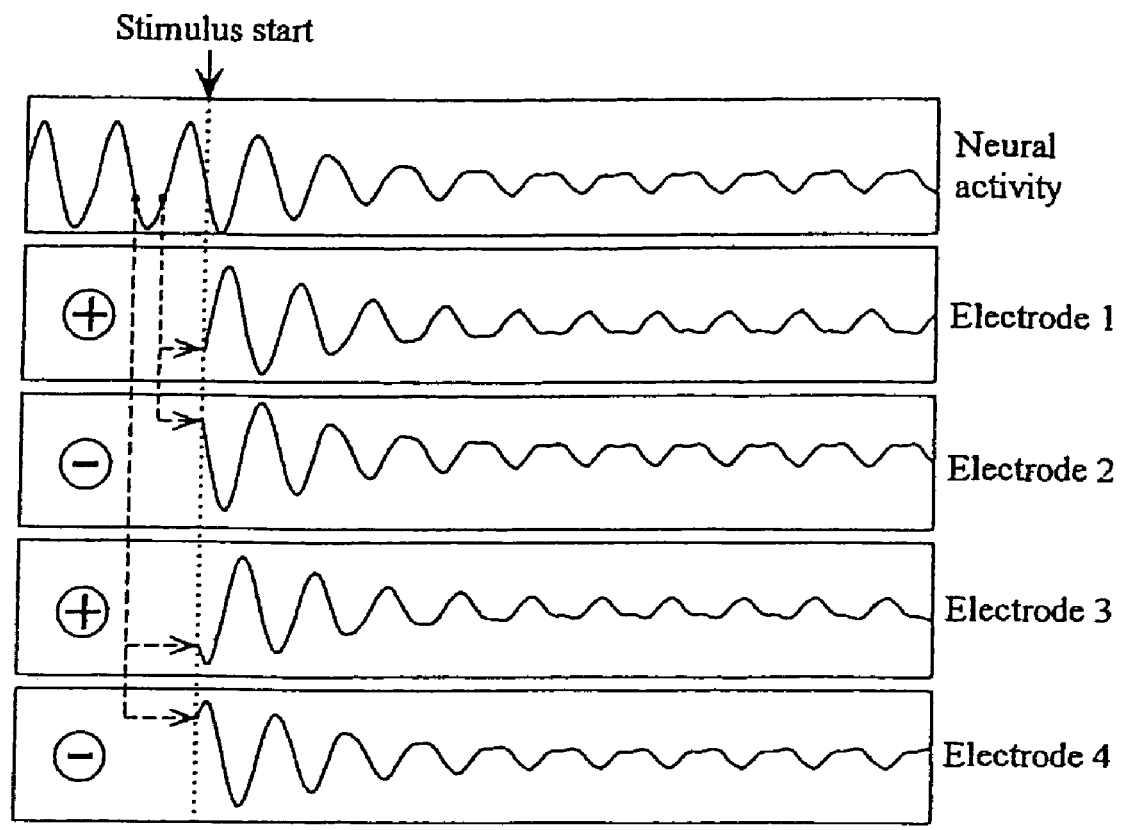
FIG. 4: shows an example of a stimulus application using 4 electrodes and two different time delays, and different polarity.
Figure 5:
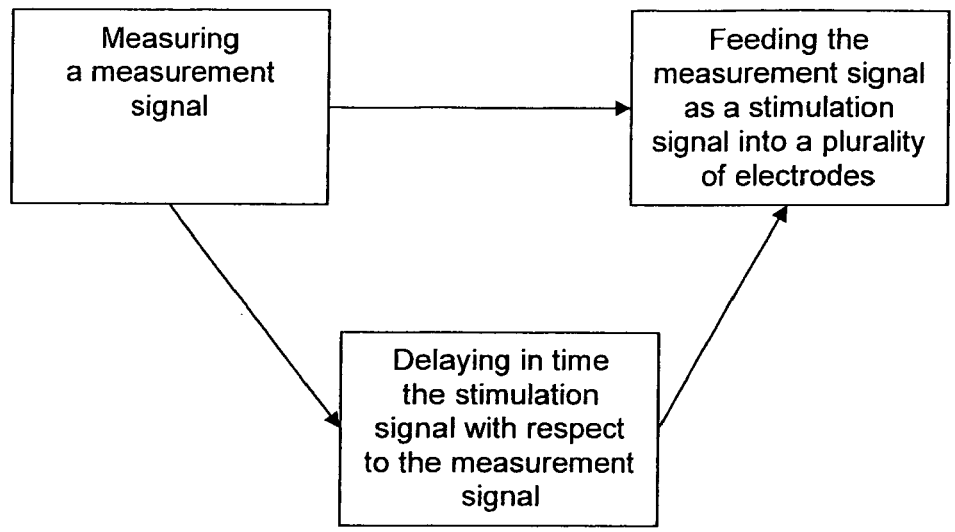
FIG. 5a: shows a flowchart illustrating a method according to an embodiment of the invention.
FIG. 5b: shows a flowchart illustrating a method according to an embodiment of the invention.
Figure 5:
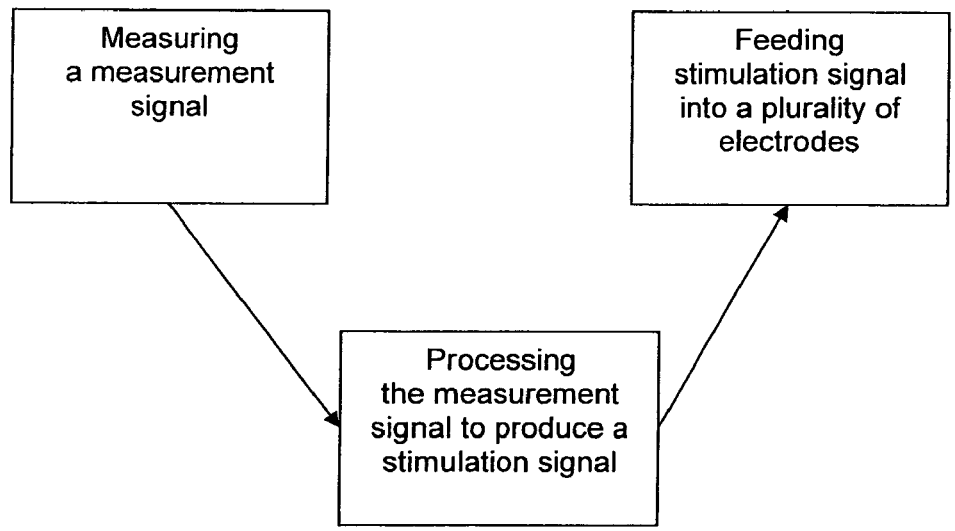

In FIG. 4, the abscissa is the time axis in seconds, while the measured neural activity and the individual stimuli, for example in the sense of the applied current, are illustrated, in each case in arbitrary units, on the ordinate. The polarity of the individual stimuli can also be varied, as an alternative to variation of the time delays. For example, a stimulation stimulus with the same time delay but with different polarity can be applied via the first two electrodes 2. In a corresponding manner, a stimulation stimulus with a different time delay but with a different polarity is applied via the third and fourth electrodes 2. The respective polarity of the individual stimuli is indicated by the symbols "+" and "−".

Figure 1:
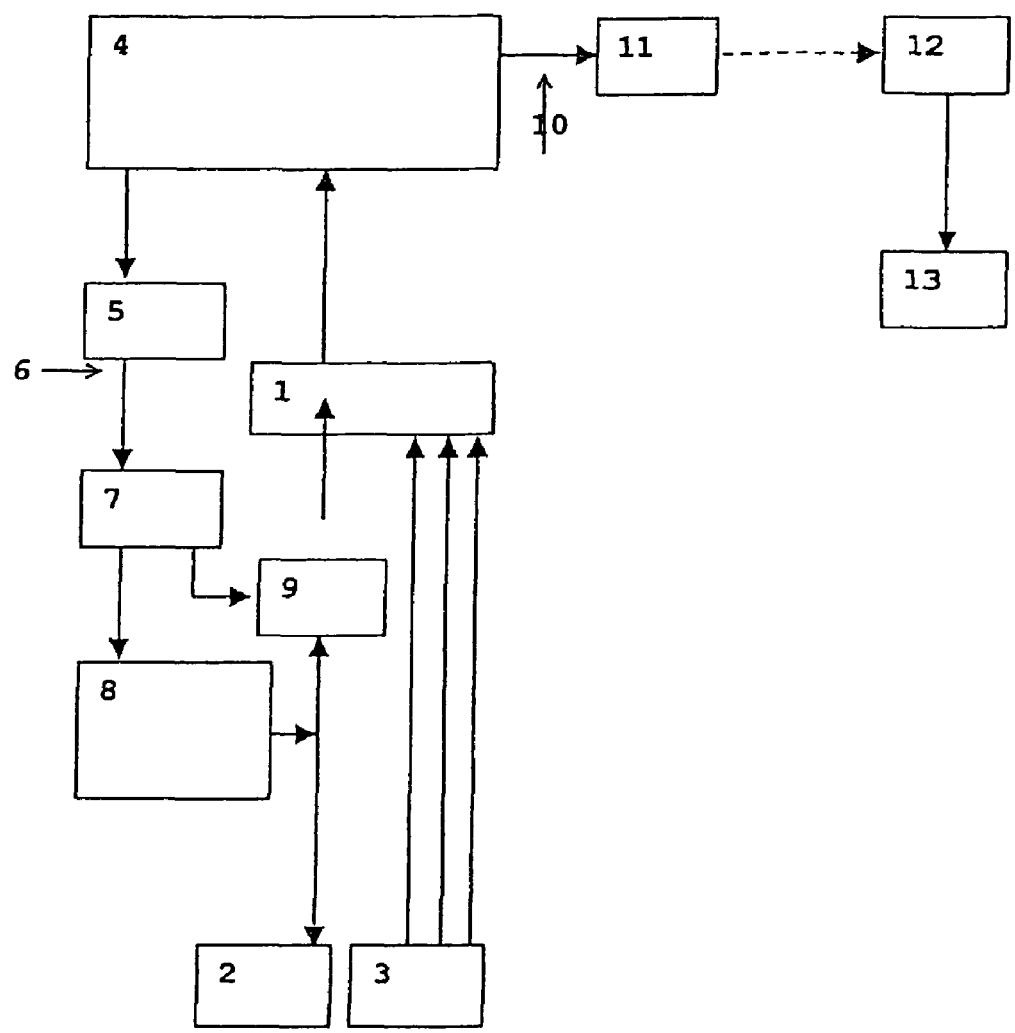
FIG. 1: shows an apparatus according to the invention.

The apparatus shown in FIG. 1 comprises an isolation amplifier 1 to which at least two electrodes 2 as well as at least one sensor 3 are connected in order to detect physiological measurement signals. The isolation amplifier is also connected to a unit 4 for signal processing and control, which is connected to an optical transmitter for the stimulation 5. The optical transmitter 5 is connected via optical waveguides 6 to an optical receiver 7, which is connected to a stimulator unit 8 for signal production. The stimulator unit 8 for signal production is connected to at least two electrodes 2. A relay 9 or a transistor is located in the input area of the electrodes 2 into the isolation amplifier 1. The unit 4 is connected via a line 10 to a telemetry transmitter 11, which is connected to a telemetry receiver 12 which is located outside the appliance to be implanted and to which a means for visualization, processing and storage of the data 13 is connected. By way of example, epicortical electrodes, deep electrodes, brain electrodes or peripheral electrodes may be used as sensors 3.

The electrodes 2 each comprise at least two wires, to whose ends a potential difference is applied for stimulation purposes. These may be macro-electrodes or micro-electrodes. Alternatively, the electrodes 2 may also each be individual wires. In this case, a potential difference is in each case applied for stimulation purposes between an individual wire and the metallic part of the housing of the generator. In addition, but not necessarily, a potential difference can be measured across the electrodes 2 in order to detect pathological activity. In a further embodiment, the electrodes 2 may also comprise more than two individual wires, which can be used both for the determination of a measurement signal in the brain and for stimulation purposes. By way of example, four wires may be accommodated in one conductor cable, in which case a potential difference can be applied or measured between different ends. This makes it possible to vary the magnitude of the derived or stimulated target region. The number of wires from which the electrode is formed is limited in the upward direction only by the thickness associated with it of the cable to be inserted into the brain, with the aim of damaging as little brain material as possible. Commercially available electrodes comprise four wires, although the electrodes may also have five, six or more wires, or else only three wires.

In a situation where the electrodes 2 comprise more than two wires, at least one of these wires may also act as a sensor 3, so that this results in an embodiment in which the electrodes 2 and the sensor 3 are combined in a single component. The wires of the electrodes 2 may have different lengths, so that they can penetrate to different brain depths. If the electrodes 2 comprise n wires, where n is an integer, then stimulation can be carried out via at least one pair of wires, in which case any sub-combination of wires is possible in order to form pairs. In addition to this component, it is also possible to provide sensors 3 which are not physically combined with the electrodes 2.

By way of example and in plain words, the apparatus according to the invention is used, in a first step, to measure the neural activity by means of the sensors. In a second step, the stimulation signals are generated by means of a time delay and if required by means of further processing of the neural activity. These stimulation signals are then used via at least two implanted electrodes for stimulation, preferably with different time delays, in a third process step. This stimulation results in desynchronization in the stimulated tissue. Details of the method of operation of the apparatus according to the invention are explained in Section 1.

As described in Section 6, the apparatus according to the invention can be implemented in various embodiments of the time control for stimulus application. The variants of time control for stimulus application are permanent, repetitive and demand-controlled stimulus application.

The permanent stimulus application according to the invention is one simple embodiment of the apparatus according to the invention which operates without any additional demand control and applies stimuli permanently, as described in Section 6.1. Permanent stimulus application therefore represents an embodiment of the apparatus according to the invention which can be implemented easily. At the same time, the self-regulating demand control according to the invention as described in Section 5 provides a good desynchronizing effect of permanent stimulation with little energy being introduced into the target population.

In the case of the repetitive stimulus application according to the invention, the apparatus according to the invention has a controller which is programmed such that it applies the stimulation signals to the electrodes 2 only during specific time intervals. There is no stimulation outside these time intervals. The control unit 4 is thus programmed such that, in the embodiment of the repetitive stimulation as described in Section 6.2 a stimulation signal which is generated with a duration that is calculated by the control unit 4 is generated at times which preferably follow one another periodically and are determined by the control unit 4, with this stimulation signal being emitted to the electrodes 2. As in the case of permanent stimulus application, self-regulating demand control of the amplitude of the stimulation signal also takes place in repetitive stimulus application.

In the case of the demand-controlled stimulus application according to the invention, the apparatus according to the invention has an additional demand controller. For this purpose, the apparatus according to the invention is preferably equipped with means which identify the signals of the electrodes 2 and/or of the sensors 3 as pathological and, when a pathological pattern is present, emit stimuli via the electrodes 2 which result in the pathological neural activity in the subpopulations that are stimulated by the individual electrodes 2 being desynchronized, and thus coming closer to the natural, physiological activity. The pathological activity differs from the healthy activity by a characteristic change in its pattern and/or its amplitude and/or its frequency content. The means for identification of the pathological pattern are in this case a computer, which processes the measured signals from the electrodes 2 and/or from the sensor 3 and compares them with data stored in the computer. The computer has a data storage medium which stores data and can be used in accordance with Sections 6 and 7 for calibration and/or control purposes. For example, the control unit 4 may comprise a chip or some other electronic apparatus with comparable computation power.

Depending on the occurrence and the extent of pathological features in the processed neural activity, a stimulus signal is emitted to the electrodes 2 in the embodiment of the demand-controlled stimulus application as described in Section 6.3, thus resulting in stimulation of the brain tissue. The apparatus according to the invention has means for identification of the occurrence and/or of the extent of the pathological features in the neural activity as measured by means of the sensor 3. The control unit 4 is programmed such that, in the embodiment of the demand-controlled stimulus application as described in Section 6.3, a stimulation signal is generated at a time defined by the control unit 4, and is emitted to the electrodes 2. Overall, the aim is to store all of those parameters that are relevant for the respective procedure for the apparatus according to the invention, relating to the nature and intensity of the stimuli, together with their time delays as well as information relating to the electrode-specific application, as well as those measured values which are relevant for the demand-controlled methods of operation and have been determined by means of the sensor 3, or parameters derived from them.

The control unit 4 preferably drives the electrodes 2 in the following manner: the control data is passed on from the control unit 4 to an optical transmitter for stimulation 5, which drives the optical receiver 7 via the optical fiber 6. Optical injection of the control signals into the optical receiver 7 provides DC isolation between the stimulation controller and the electrodes 2. This means that this prevents interference signals from the unit for signal processing and the controller 4 from being injected into the electrodes 2. By way of example, a photocell may be used as the optical receiver 7. The optical receiver 7 passes on to the stimulator unit 8 the signals which are input for the stimulation 5 via the optical transmitter. Specific stimuli are then passed on via the stimulator unit 8 and via the electrodes 2 to the target region in the brain. In the situation where the electrodes 2 are also used for measurement purposes, a relay 9 is also driven from the optical transmitter for stimulation 5 via the optical receiver 7, thus preventing the injection of interference signals. The relay 9 or the transistor ensures that the neural activity can be measured again immediately after each stimulus, without overdriving the isolation amplifier. The DC isolation need not necessarily be provided by optical injection of the control signals and, in fact, other alternative control processes can also be used. These may, for example, be acoustic inputs, for example in the ultrasound band. Interference-free control can also be achieved, for example, with the assistance of suitable analog or digital filters.

Furthermore, the apparatus according to the invention is preferably connected to means for visualization and processing of the signals, and for data back-up 13, via the telemetry receiver 12. In this case, the unit 13 may comprise the methods mentioned in the following text for data analysis.

Furthermore, the apparatus according to the invention may be connected via the telemetry receiver 13 to an additional reference database in order, for example, to monitor correct operation of the appliance and, possibly, to design the control mechanisms as described in Section 7.2 to be more efficient, by modification of the parameters.

The stimulation mechanism is explained in detail in Section 1. Section 2 contains a definition of the most important terms. The process steps for measurement of the neural activity via their processing as far as the generation of the overall stimuli is explained in Section 3. The physical arrangement of the electrodes and sensors is the subject matter of Section 4. Section 5 deals with the self-regulating demand control of the stimulation amplitude. The control of the stimulus application and the calibration and adaptation of the stimulation parameters are described in Sections 6 and 7. The advantages of the apparatus according to the invention are described in Section 8.

1 Stimulation Mechanism

The aim of the stimulation is to counteract illness-dependent synchronization in a nerve cell population, by desynchronization. This is done by applying stimuli at at least two points, which stimuli are generated by measuring the neural activity, by converting this to a stimulation signal on the basis of a processing step which may be provided, and by application, preferably with a time delay, so that, surprisingly, this results in desynchronization. The desynchronizing effect of the stimulation is assisted by the illness-dependent interaction between the neurons and the decrease in the stimulation effect with the distance between the stimulated tissue and the electrode. In plain words, the energy of the system to be influenced is utilized in order to achieve a therapeutic effect with minimal intervention. The apparatus according to the invention changes the nerve cell population to be desynchronized directly to a desynchronized state. The desired state, that is to say complete desynchronization, typically occurs within a few periods of the neural activity, frequently in less than one period.

There is typically a need for permanent or repetitive stimulation, since the nerve cell population to be desynchronized becomes resynchronized again, from experience, once the stimulation is switched off. Since the stimulation is directly related to the neural activity of the target area, or of an associated area, the stimulation amplitude is automatically minimized after successful desynchronization. This is made possible by using the feedback stimulation signal, that is to say the processed neural activity, as the stimulation stimulus, that is to say the extent of synchronization permanently controls the intensity of the stimulation. This process works for a wide range of stimulating parameters which can be modified, such as the stimulation period T, the time delay and the intensity, does not require any complex calibration, and has a high degree of tolerance to faults and errors. Furthermore, the amount of energy which is introduced into the tissue to be desynchronized is minimized because of the direct relationship between neural activity and the stimulation pattern, thus leading to the expectation of reduced side-effects.

The apparatus according to the invention and its operation will be explained using examples in the following text.

The apparatus according to the invention and the controller are equipped with means which can carry out all of the steps of the treatment process according to the invention. The disclosed method steps are thus also intended to implicitly disclose means for carrying out the method step. The method steps thus also at the same time represent the functionalized apparatus features.

According to the invention, the electrodes are introduced into the brain region which is responsible for the creation of the clinical signs. According to the invention, at least two or preferably four or else three or more electrodes are introduced either directly into the region or into one or more nerve cell populations or nerve fiber groups which are linked to this region. The number of electrodes is restricted only by the need to ensure that there is not an unrestricted density of electrodes in one brain region, in order that the tissue is not unnecessarily damaged and, in particular, to reduce the risk of bleeding on insertion of the electrodes. In any case, the number of electrodes introduced into the region should be N, where $N \geq 2$.

In this case, each electrode emits a signal in its surrounding area, which, while propagating either directly in its surrounding area or via a nerve fiber group, results in desynchronization in a different area. In order to achieve desynchronization, the measured and processed neural activity is used as a stimulation stimulus, in each case with a time delay, see Section 3. The apparatus according to the invention thus has a controller which drives at least two electrodes 2 such that they produce desynchronization in the area relatively closely surrounding them and/or by passing on the stimulation via a fiber group in another brain area.

According to the invention, N electrodes, where $N \geq 2$, are preferably driven such that there is a time delay of T/N between the individual electrode signals, assuming that the stimulating electrodes 2 are in the area to be desynchronized. In this case, as described below, T is the period of the rhythmic neural activity to be desynchronized. If at least one of the stimulating electrodes 2 is not located in the area to be desynchronized, the delay time between the stimulus location and the location of the neuron population which is influenced in this way must be taken into account in the drive for an electrode 2 such as this. This is described in Section 7.3. The apparatus according to the invention accordingly has a controller which, in the case of N electrodes, preferably produces a stimulation signal which is shifted in time through essentially one N-th of the period of the activity to be desynchronized. The time shift is in this case preferably essentially equidistant.

Surprisingly, in the case of this equidistant time shift of the neuron populations which are each influenced by the N electrodes 2 this does not simply result in the neuron population being subdivided into N sub-populations which are each synchronized in their own right. In fact, this stimulation surprisingly leads to desynchronization of the entire neuron population to be desynchronized, thus leading to suppression of the pathological symptoms. If at least one electrode 2 is located outside the area to be desynchronized, then the effects of the indirect stimulation must be taken into account, as described in Section 7.3.

The new method and the new apparatus result in the desynchronization being achieved in a qualitatively different manner to that in the prior art cited above. Instead of acting specifically on the illness-synchronous nerve cell group in a vulnerable phase of its rhythm, the relevant nerve cell group is simply stimulated on a time-coordinated basis at a plurality of locations, see Section 3.3, in such a manner that desynchronization occurs. The neural activity process as described in Section 3.2 at the individual stimulus locations is used for this purpose. Stimulation must be applied to at least two, and preferably more than two, stimulus locations. The desynchronization that surprisingly occurs is assisted by the interaction, which is increased by the illness, between the neurons and by the stimulation effect which decreases with the distance between the stimulation location and the neuron to be stimulated. In this case, use is made of an effect mechanism which is responsible for the illness-related synchronization. In plain words, the energy of the system to be influenced is utilized in order to achieve a therapeutic effect with minimal intervention. The best results are achieved when overall stimuli with essentially equidistant time delays are used. However, treatment successes are also achieved when the time delays between the stimuli emitted via the electrodes 2 are not equidistant. In a case such as this, at least partial desynchronization is achieved. The treatment results become better the closer the chosen time delays become to equidistant time delays.

2 Definition of Terms

Target Population:

In the following text, the expression target population means the nerve cell population which is directly stimulated by an implanted stimulation electrode.

A target population is stimulated directly by means of an electrode which is implanted in it or close to it.

The nerve cell population which is synchronously active as a result of the illness is referred to as the area to be desynchronized, as the nerve cell population to be desynchronized, or as the neuron population to be desynchronized. The area to be desynchronized is not associated with anatomical boundaries. In fact, this can also be understood as meaning at least one component, comprising the following group:

at least a part of at least one anatomical area, at least one complete anatomical area.

The area to be desynchronized may be stimulated either directly or indirectly.

Direct Stimulation:

In this case, the stimulation electrode 2 is located directly in the area to be desynchronized.

This electrode 2 in this case influences the target population which is located in the area to be desynchronized.

Indirect Stimulation:

In this case, the area to be desynchronized is not stimulated directly by means of the stimulation electrode 2. In fact, a target position or a fiber group which is functionally closely linked to the area to be desynchronized is stimulated via the electrode 2. In this case, the stimulation effect preferably propagates to the area to be desynchronized via anatomical links. The expression target area is introduced as a generic term for the target population and the fiber group, for indirect stimulation. In the following text, the expression target area should be understood as the neuron population, which is functionally closely linked to the area to be desynchronized, and the connecting fiber group, which are directly stimulated by implanted electrodes 2.

Neural Activity:

The description of the mechanism of the apparatus according to the invention is based essentially on the term neural activity. The neural activity of the neuron population to be desynchronized and/or of a neuron population which is closely linked to it is measured, stored, and processed in accordance with Section 3.2, and is used as a stimulation signal, thus providing the self-regulating demand control according to the invention. In the following text, the expression the measured neural activity of the neuron population to be desynchronized means a signal which reproduces the time development of the activity of the neuron population to be desynchronized. By way of example, local field potentials can reproduce the time development of the activity of the neuron population to be desynchronized. The neural activity can preferably be measured directly in the area to be desynchronized, although it is also possible to measure an activity which is associated with the neural activity of the area to be desynchronized, for example a different brain area, in this case by way of example the motor cortex, or the activity of a muscle group which is controlled by the area to be desynchronized. In a further embodiment of the apparatus according to the invention, neural activities are measured at different locations and are combined in order to obtain an adequate representation of the neural activity of the neuron population to be desynchronized. These variables which are associated with the neural activity of the area to be desynchronized are also referred to as neural activity in the following text.

Feedback Stimulation Signal:

The expression feedback stimulation signal means that signal which, according to Section 3.2, represents the measured and processed neural activity and is used as the basis for the individual stimuli.

Rhythm:

The expression rhythm is used to mean the rhythmic, that is to say approximately periodic, neural activity which results from nerve cell activity that is excessively synchronous because of an illness. A rhythm can occur briefly or on a long-lasting basis.

Period:

One central term for the apparatus according to the invention is the period of the rhythmic neural activity, and this is used as a time reference for the application of the individual stimuli. Adaptation of the stimulation T, as described in Section 7.2.1, preferably results in the period of the rhythmic neural activity matching the stimulation period T.

Time Delay:

The apparatus according to the invention causes signals to be passed to the stimulation electrode 2 which correspond to the neural activity, as measured in accordance with Section 3.1 and possibly processed, relating to an earlier time. This time shift is referred to in the following text as the time delay and represents one important stimulation parameter, which is related to the period of the rhythmic neural activity.

Individual Stimulus:

The expression an individual stimulus, see Section 3.3, in the following text means a stimulation stimulus which is applied via a single electrode and acts over a time interval. The neural activity processed in accordance with Section 3.2 is used for these stimulation stimuli.

Overall Stimulus:

An overall stimulus is the totality of the individual stimuli applied via the electrodes, see Section 3.4.

3 Nature of the Stimulation Stimulus 3.1 Measurement of the Neural Activity

The time profile of the neural activity of the area to be desynchronized can be measured directly or indirectly by means of the sensors 3.

The sensors 3 (see FIG. 1) are located in the brain and/or outside the brain. In the brain, they are positioned in the area to be desynchronized and/or in at least one other area which is functionally linked to it. Outside the brain, the sensors 3 are located at body parts which are linked to the neural activity that is synchronized because of the illness, for example as electrodes on a trambling muscle. The measurement signals of the neural and/or non-neural, for example muscular, activity are processed in a unit for signal processing 4, and are stored. In this case, these measurement signals can be processed and stored permanently and/or at discrete time intervals. In the latter case, the duration and/or the intervals between the discrete measurement intervals are/is determined by means of a deterministic and/or stochastic algorithm.

3.2 Processing of the Neural Measurement Signals

The measurement signals which are stored in the unit for signal processing 4 are then processed in order to be made available as stimulation signals. The following processing steps may be carried out:

1. The measured neural activity may be filtered, for example bandpass filtering may be carried out on the neural activity. The filtering may be necessary when activity which is not yet illness-specific, for example from other neuron populations, is additionally measured in addition to the illness-specific activity by means of the sensor 3. Since the illness-specific activity typically occurs in a frequency range which differs from the frequency range of non-illness-specific activity, the activity in the illness-specific frequency range is preferably determined in this case. This is done, for example, by means of a frequency analysis. It may likewise be necessary to carry out a wavelet analysis and/or a Hilbert transformation and/or filtering in the time domain.

2. When the neural activity of the neuron population to be desynchronized is measured by means of a plurality of sensors 3, then a linear and/or non-linear combination and/or transformation can be carried out, for example multiplication, addition or calculation of a function, of the measured neural activity.

3. The measured neural activity is delayed in time. The time delays which are used for this purpose are defined in Sections 3.3 and 3.4 and also, in accordance with Section 7.3, take account of the position of the stimulation electrodes with respect to the neuron population to be desynchronized. Furthermore, the time delays can preferably be adapted during the stimulation, in accordance with Sections 7.2.1 and 7.2.2.

4. The measured neural activity is amplified. The measured neural activity is several orders of magnitude less than the stimulation amplitudes which, from experience, lead to a stimulation effect. Amplification must therefore be carried out, and can be adapted in accordance with Section 7.2.3 during the stimulation.

5. Since signals with high gradients have a major effect on the neural dynamics, the measured neural activity is coded, for example, in the form of pulse trains or high-frequency pulse trains comprising short square-wave pulses. Other coding methods can also be used in order to increase the stimulation effect.

6. The polarity of the neural activity is changed. By way of example, this has been used for the overall stimulus sketched in FIG. 4.

7. The maximum amplitude of the stimulation signal is restricted.

8. The measured neural activity is in contrast transformed so as to produce stimulation signals whose net charge introduced is essentially zero.

Except for item 3, items 1, 2 and 4 to 6 can be used optionally.

The processed neural activity is determined by the use of any desired combination of the processing steps mentioned above.

3.3 Form of the Individual Stimuli

In the following text, the expression an individual stimulus means a stimulation stimulus which is applied via a single electrode and acts in a time interval. The feedback stimulation signal, that is to say the neural activity processed in accordance with Section 3.2, is used for these stimulation stimuli.

In this case, the expression time-coordinate stimulation means, by way of example, that the individual stimuli are applied via the respective electrode 2 with respectively suitable time delays, preferably different time delays, and also for a different duration—as described in Section 3.4—in order to produce desynchronization between the stimulated sub-populations and within the sub-populations of the neuron populations to be desynchronized. The time delays are stated, for example, as fractions of the period of the oscillatory neural activity to be desynchronized and are preferably essentially a multiple of one N-th of the period, where N is a small integer, for example 4. N is in this case an integer, preferably below 1000, particularly preferably less than 100 and in particular less than 10.

The time delays of the individual stimuli can also be chosen, for example, to be greater than the stimulation period T. For this purpose, the apparatus according to the invention has means which apply the described electrical stimulation stimuli in the described manner. The means are electrodes 2, and a controller 4 which emits control signals to be electrodes 2 in order to emit these stimuli. Furthermore sensors 3 and the unit for signal processing 4, which records the neural activity and prepares for the further use as stimulation stimuli. The individual stimuli which are applied via the electrodes 2 are referred to as the overall stimulus, and achieve desynchronization in the neuron population to be desynchronized on the basis of the active mechanism of the apparatus according to the invention.

Examples of overall stimuli are shown in FIGS. 3 and 4. One individual stimulus is preferably emitted via each electrode in the course of one overall stimulus.

If overall stimuli are applied repetitively, the electrodes 2 which are driven in the course of an overall stimulus may be varied. In particular, the subset of the electrodes 2 which are driven for the respective overall stimulus can be selected by means of a stochiostic and/or deterministic algorithm.

3.4 Pattern of the Overall Stimuli

In the course of the application of an overall stimulus, one individual stimulus is applied via at least two stimulation electrodes 2, but preferably via each individual stimulation electrode 2. Overall stimuli are preferably generated whose net charge introduced is essentially zero. The individual stimulus may assume the forms described in Section 3.3.

The individual stimuli which are applied via the various electrodes 2 may but need not be different in terms of the nature and/or intensity, for example governed by the gain. For this purpose, the apparatus according to the invention has a controller which is programmed such that it can vary the nature and/or the intensity of the individual stimuli. The nature and the intensity of the individual stimuli are governed by the parameters which are used for the processing steps as described in Section 3.2.

By way of example, in the case of direct stimulation via N electrodes 2, the same individual stimulus, in the form of the same processed neural activity in accordance with Section 3.2, can in each case be applied with a difference in the time delay of in each case T/N, where T is the stimulation period. By way of example, the same continuous stimulation stimuli can be administered via the first, second, third and fourth electrodes 2 for N=4 with time delays which are in each case shifted by T/4, as is illustrated in FIG. 3.

For this purpose, the apparatus according to the invention has a controller which is programmed such that it drives N electrodes 2 with individual stimuli, whose time delays are essentially a multiple of T/N.

As a further example, time delays for the stimulus application can be replaced by changing the polarity of the individual stimuli. For this purpose, the apparatus according to the invention has a controller which is programmed such that it can drive at least one of the electrodes 2 with a changing polarity in each case. For example, for N=4, one pair of individual stimuli of opposite polarity can in each case be applied via the first and the second electrode 2, and with a time delay of T/4 via the third and the fourth electrode 2, as shown in FIG. 4.

As an alternative to this, by way of example, particularly in the case of the demand-controlled stimulus application as described in Section 6.3, the time delays and/or the polarity and/or the application duration and/or the intensity of the individual stimuli within an overall stimulus may be varied systematically or on a randomly controlled basis, that is to say on the basis of a deterministic or stochastic rule. For this purpose, the apparatus according to the invention has a controller which is programmed such that it drives the time delays and/or the polarity and/or the application duration and/or the intensity of the individual stimuli within an overall stimulus deterministically and/or stochastically.

By variation of the time delays and/or the polarity and/or the application duration and/or the intensity of the individual stimuli within the overall stimuli, it is possible to prevent adaptation processes in the neuron populations which result in an increase in the stimulation intensity in order to achieve the same therapeutic effect.

4 Number and Spatial Arrangement of the Electrodes and Sensors

4.1 Number of Stimulation Electrodes

The number of electrodes 2 is a compromise between two opposing aims:

On the one hand, the neuron population to be desynchronized should be split into as many functional sub-populations as possible by the stimulation. This is achieved to a greater extent the greater the number of electrodes used for stimulation. On the other hand, the number of electrodes to be implanted should be kept as small as possible in order to prevent unnecessary tissue damage and, in particular, brain bleeding during the implantation. At least two electrodes may be used. By way of example, it is also possible to use three electrodes. It is particularly preferable to use four electrodes, since the desynchronization is more pronounced and longer lasting when using four electrodes. If the number of electrodes is increased to five or up to 100 or more, the desynchronization effect is improved in terms of the extent and duration. The use of a greater number of electrodes may be feasible, for example, when micro-electrodes and/or modern neurochip technologies are used.

4.1.1 Embodiment for the Situation in which all the Electrodes 2 are Positioned in the Nerve Cell Population to be Desynchronized The N electrodes, where N is an integer greater than 1, should preferably be arranged such that approximately one N-th of the nerve cell population to be desynchronized can be stimulated by each individual electrode. This can be achieved with a different number of electrodes and with a different geometric arrangement of the electrodes with respect to one another. By way of example, it is possible to choose any desired asymmetric arrangement. However, essentially symmetrical arrangements are preferable, particularly when a small number of stimulation electrodes are being used since, in this case, it is possible for the same distances to occur between the electrodes, thus allowing the stimulation-dependent functional splitting into equivalent sub-populations with the least amount of power being introduced. By way of example, the end points of the electrodes, projected along the electrodes, may essentially form a square. By way of example, it is also possible to use six electrodes. In this case, four are preferably arranged essentially in a square on one plane, while the other two are located essentially equidistantly at right angles to this plane, with their connecting line essentially forming the axis of rotation of the four electrodes which are arranged in a square. At least some of the electrodes may also have different lengths in order to produce different geometric arrangements. According to the prior art, it is possible to combine a plurality of stimulation electrodes in one stimulation electrode to be implanted, for example by positioning the stimulation contacts at different distances from the end of the electrode. This makes it possible to achieve the same stimulation effect with a small number of electrodes to be implanted, thus further reducing the occurrence of brain damage.

4.1.2 Embodiment for the Situation in which at Least One Electrode 2 is not Positioned in the Nerve Cell Population to be Desynchronized In this stimulation form, stimulation is carried out in at least one target area, which is different from the area to be desynchronized. In this case, the indirect stimulation can be carried out by stimulation of a neuron population which is not the same as the nerve cell population to be desynchronized, and/or by stimulation of a fiber group which is linked to the nerve cell population to be desynchronized. In this case, either at least one electrode 2 or a multiple electrode arrangement as described in Section 4.1.1 can be used in a target area, for example in the area to be desynchronized.

4.2 Number of Sensors

The mechanism of the apparatus according to the invention essentially comprises, as described in Sections 1 and 3, the measured and processed neural activities of the neuron population to be desynchronized being applied again as stimulation. The sensors 3 are one of the most important components of the apparatus according to the invention and, as described in Section 3.1, may be positioned either outside the neuron population to be desynchronized or preferably directly in the neuron population to be desynchronized. Only one sensor 3 is preferably used, in order to detect the activity of the neuron population to be desynchronized. This keeps the number of sensors to be implanted as small as possible, in order to prevent unnecessary tissue damage and, in particular, brain bleeding during the implantation. However, for example, it is also possible to use two or more sensors in order to reconstruct the neural activity of the neuron population to be desynchronized much more completely as a combination of the measured activities.

Furthermore, possible brain damage caused by the implantation is further reduced or avoided, and the stimulation effect is improved, by combining the sensors 3 and stimulation electrodes 2 in one electrode to be implanted.

4.2.1 Embodiment for the Situation in which the Sensors 3 are all Positioned in the Nerve Cell Population to be Desynchronized The sensors 3 should preferably be arranged such that a large proportion of the nerve cell population to be desynchronized can be detected by means of the sensors. This can be achieved with a different geometric arrangement of the sensors with respect to the tissue to be desynchronized. In the case of an arrangement with only one sensor 3, this may be located, for example, in the center of the tissue. In the case of arrangements having a plurality of sensors, as described in Section 4.1.1, the sensors may be arranged in a similar manner to that which has been described for the stimulation electrodes.

4.2.2 Embodiment for the Situation in which at Least One of the Sensors 3 is not Positioned in the Nerve Cell Population to be Desynchronized In this form of the activity measurement, an activity which is associated with the neural activity of the neuron population to be desynchronized is measured in at least one area which is not the same as the area to be desynchronized. In this case, as described in Section 3.1, the indirect measurement can be carried out by measurement of the activity of a neuron population which is not the same as the nerve cell population to be synchronized and/or of a fiber group and/or of a body part which is linked to the nerve cell population to be desynchronized.

5 Self-Regulating Demand Control of the Stimulation Amplitude

One of the most important characteristics of the mechanism of the apparatus according to the invention is self-regulating demand control of the amplitude of the stimulation signal which is applied to the area to be desynchronized. The described self-regulation is carried out by the applied individual stimuli comprising the processed neural activity. When there is relatively strong synchronous activity in the area to be desynchronized, a large variance can be expected in the measured neural activity, as is known to those skilled in the art. This leads directly to a time-delayed stimulation according to the invention, with an increased stimulation amplitude. After achieving desynchronization, only neural activity with a small variance will be expected, as a result of which the stimulation amplitude is directly influenced, and is automatically reduced. If resynchronization occurs again, then the apparatus according to the invention can automatically take account of the increased requirement for desynchronizing stimulation, by the greater variance in the neural activity leading to the formation of stronger individual stimuli. This represents self-regulating demand control of the apparatus according to the invention, see also FIG. 2c.

The mechanism on which the self-regulating demand control is based is used in all the embodiments of the apparatus according to the invention that are described in more detail in the following text.

6 Control of the Stimulus Application

The expression time control of the stimulus application means an embodiment of the apparatus according to the invention which is preferably programmed in advance, with the overall stimuli being applied in the specific manner by means of the stimulator unit 8. The variants of time control of the stimulus application are permanent, repetitive and demand-controlled stimulus application. In addition, manual demand control can be implemented, for example for a stimulus application carried out by the patient or by the doctor.

6.1 Permanent Stimulus Application

In the case of permanent stimulus application, the apparatus according to the invention has a controller which is programmed such that it continuously applies the stimulation signals to the electrodes 2. Permanent stimulus application represents the simplest embodiment, which is the easiest to implement, of the apparatus according to the invention. At the same time, the self-regulating demand control according to the invention as described in Section 5 results in a good desynchronizing effect of permanent stimulation while introducing little energy into the target population.

During permanent stimulus application, the intensity parameters can be adapted in accordance with Section 7.2.3. In the same way, the time parameters—the stimulation period T and/or time delays—can be adapted during permanent stimulation in accordance with Sections 7.2.1 and 7.2.2 in conjunction with adaptation of the stimulation intensity, or independently of it.

6.2 Repetitive Stimulus Application

In the case of repetitive stimulus application, the apparatus according to the invention has a controller which is programmed such that it applies the stimulation signals to the electrodes 2 only during specific time intervals. There is no stimulation outside these time intervals.

In the case of repetitive stimulus application, the overall stimuli can be administered on a strictly periodic time basis or on a non-periodic time basis. In this embodiment, the apparatus according to the invention has a controller which is programmed such that it periodically and/or non-periodically monitors the time intervals between the stimulation intervals and/or the duration of the intervals. A sequence of overall stimuli which is not periodic in time can be generated by means of a stochastic and/or deterministic algorithm, in order to achieve the desired desynchrohized state of the population to be desynchronized. The stimulation and measurement intervals may be arranged such that they overlap, occur at the same time, or occur at separate times.

During repetitive stimulus application, the intensity parameters can be adapted in accordance with Section 7.2.3. In the same way the time parameters—the stimulation period T and/or time delays—can be adapted during repetitive stimulation in accordance with Sections 7.2.1 and 7.2.2 in conjunction with adaptation of the stimulation intensity, or independently of it.

6.3 Demand-Controlled Stimulus Application

In the case of demand-controlled stimulus application, the apparatus according to the invention has a controller which is programmed such that it switches the stimulation signals on and off in a manner corresponding to the specific states of the neuron population to be desynchronized. By way of example, the stimulation is switched on as described in the following text.

The activity of the neuron population to be desynchronized is measured by means of the sensor 3. The neural activity is passed to the unit 4 for signal processing and/or closed-loop control which, inter alia, acts as means for identification of a pathological feature. As soon as the unit 4 for signal processing and/or closed-loop control identifies a pathological feature in the neural activity, the application of an overall stimulus is started. As soon as the pathological feature disappears as a result of the effect of the applied stimulation, stimulation is preferably switched off. In one possible embodiment as a unit 4 for signal processing and/or open-loop/closed-loop control, the apparatus according to the invention therefore has a computer which contains a data storage medium, in which the data relating to the clinical signs is stored and is compared with the measurement data. The expression the data relating to the clinical signs means parameters and measurement variables which are relevant for the stimulation, for example the instantaneous frequency of the neural activity measured by means of the sensor 3, of the threshold value which is required for the procedure for demand-controlled stimulus application, and the stimulation parameters which define the stimulus intensity. The expression a pathological feature means, for example, illness-dependent synchronization of the neuron population to be desynchronized, and can be identified by the following characteristics of the neural activity:

a) If the pathological activity of the neuron population to be desynchronized and/or of a neuron population which is closely linked to this neuron population and/or a closely linked part of the nervous system or the musculature is measured exclusively or predominantly by means of the sensor 3, for example in the case of the direct measurement as described in Section 3.1 and Section 4.2.1, the neural activity is used directly to determine whether the amplitude of the neural activity exceeds a threshold value. The apparatus according to the invention is thus, in one preferred embodiment, equipped with means for identification of a value of the amplitude of the neural activity corresponding to the threshold value. In this case, the neural activity itself, and/or its magnitude and/or its amplitude are/is preferably compared with the threshold value. The means for identification of the threshold value may in this embodiment be programmed such that, for example, it compares the neural activity itself and/or its magnitude and/or its amplitude with the threshold value. The amplitude is determined either in a simple version by determination of the magnitude of the signal, and/or with bandpass filtering and subsequent Hilbert transformation, or wavelet analysis. The unit 4 for signal processing and/or closed-loop control is in this case programmed such that it can determine the magnitude of the signal and/or bandpass filtering with Hilbert transformation and/or wavelet analysis. The neural activity or its magnitude is particularly preferably used, since the calculation of the amplitude involves considerably more computation effort, and the determination of the amplitude cannot be carried out on a single measured value of the neural activity but must be carried out at a sufficiently long time interval, as is known by those skilled in the art, and this can somewhat delay the identification of the pathological feature.

b) If activity which is not yet illness-specific, for example from other neuron populations, is additionally measured by means of the sensor 3 as well as this pathological activity of the neuron population to be desynchronized, for example as in the case of the indirect measurement described in Sections 3.1 and 4.2.2, a further algorithm step must be introduced during the analysis of the neural activity. Since the illness-specific activity typically occurs in a frequency range which is different from the frequency range of the non-illness-specific activity, it is preferably suitable for this purpose to estimate the activity in the illness-specific frequency range. The frequency of the illness-specific activity is determined, for example, by determination of the difference between successive trigger points. Trigger points are points such as maxima, minima, points of inflection and zero crossings. This analysis preferably carried out using a sliding time window, with the mean value of a plurality of time differences being formed, thus improving the stability. Alternatively, the frequency estimate can also be determined by spectral estimation methods and other frequency estimators, which are known to those skilled in the art. For this purpose, one particular embodiment of the apparatus according to the invention has means for estimation of the activity in the illness-specific frequency range, such as spectral estimation methods, wavelet analysis etc. This is achieved, by way of example, by means for carrying out a frequency analysis. By way of example, the spectral energy in the illness-specific frequency range can be determined using a sliding window. Alternatively, after bandpass filtering, the amplitude in the illness-specific frequency range can be determined by determination of the maximum of the bandpass-filtered signal or by determination of the mean value of the magnitude of the bandpass-filtered signal, or with subsequent Hilbert transformation or by means of wavelet analysis. For this purpose, the apparatus according to the invention has, for example, means for bandpass filtering of the amplitude and means for determination of the maximum of the bandpass-filtered signal, and/or means for determination of the mean value of the magnitude of the bandpass-filtered signal, and/or means for carrying out a Hilbert transformation and/or a wavelet analysis.

By way of example, the same overall stimulus is always used for demand-controlled stimulus application. The stimulation period T is preferably matched to the instantaneous frequency of the neuron population to be desynchronized, as described in Section 7.2.1. When the pathological feature is present, a stimulus is then applied with a stimulation period T matched to the instantaneous frequency. The time delays can likewise be adapted in accordance with Section 7.2.2, and/or the intensity of this stimulus in this case preferably remains constant. However, as in Section 7.2.3, the intensity parameters can be modified in accordance with the stimulation effect.

6.3.1 Definition of the Requirement

For at least two reasons, there is no unique relationship between the extent of the pathological feature and the extent of the illness-specific symptoms. On the one hand, the distance between the sensor 3 and the area to be desynchronized, in which the neural activity to be measured is generated, results in a change in the amplitude in the illness-specific frequency range. On the other hand, a specific extent of the illness-specific feature, that is to say the extent of the rhythmic activity in the illness-specific frequency range, is not unambiguously linked with the illness-specific symptoms. Since the illness-specific rhythm affects complex nerve networks in the brain which typically, on top of everything else, do not satisfy simple linear dynamic laws, there are no unambiguous relationships between the illness-specific rhythm and the extent of the symptoms. If, for example, the illness-specific rhythm does not sufficiently well match the biomechanically predetermined natural frequency of an extremity, the tremor which is caused by the illness-specific rhythm is considerably less than if the illness-specific rhythm were to resonantly match the biomechanically predetermined natural frequency of the extremity.

The characteristic property, such as the dominant frequency and the amplitude, of the measured neural activity are in an empirical range which is known to those skilled in the art. The value of the extent of the illness-specific feature of the neural activity measured by means of the sensor 3 is referred to as a threshold which, if exceeded, typically results in the occurrence of symptoms, for example of the tremor. The threshold is a parameter which must be chosen for the embodiment of the demand-controlled stimulus application as described in Section 6.3. The apparatus according to the invention thus has means, in the form of the control unit 4, for identification of a threshold value. The method according to the invention for demand-controlled stimulus application results in the advantage that the effectiveness of the apparatus according to the invention does not critically depend on the choice of the threshold, but there is a wide error tolerance with regard to the choice of the threshold, for example in a range of up to 50% of the maximum extent of the illness-specific feature. The choice of the threshold is determined either intraoperatively or preferably in the initial days after the operation by measurement of the neural activity by means of the sensor 3, with the extent of the illness-specific feature being determined, and being compared with the extent of the symptoms, for example the intensity of the tremor.

In a less preferred embodiment of the demand-controlled stimulus application, a representative value, for example the mean value, of a range of a threshold values measured in patients is adopted as the threshold.

In one preferred embodiment, the choice of the threshold is checked essentially at regular intervals, for example in the course of six-monthly inspections.

In the repetitive stimulation embodiment with demand-controlled stimulus intensity as described in Section 6.2, there is no need for threshold value detection.

The three stimulation methods described above can preferably be used in a different combination with the methods for adaptation of the stimulation parameters as described in Section 7.2.

The inherent self-regulating demand control according to the invention is a common feature of all three stimulation methods. The direct relationship between the stimulation signals and the measured neural activity results in self-regulating demand control as described in Section 5, thus minimizing the amount of energy introduced into the target population. This self-regulating demand control acts independently of the implementation of the additional demand control as described in Section 6.3, and of the calibration and closed-loop control of the parameters as is described in Section 7.

7 Calibration and Adaptation of the Parameters

The following text is based on the assumption that all the electrodes 2 are located in the neuron population to be desynchronized. The situation in which at least one electrode is located outside the neuron population to be desynchronized will be considered separately at the end of the section. By way of example, a calibration and adaptation can be carried out for the following parameters of the apparatus according to the invention: the frequency of the stimulation signal, whose reciprocal corresponds to the stimulation period, the time delays of the individual stimuli, and the intensity of the individual stimuli.

7.1 Stimulation Parameters at the Start of the Stimulation
7.1.1 Frequency, Stimulation Period Choice of the frequency without previous operation of the apparatus: the frequency range of the pathological neural activity for the respective clinical signs is known to those skilled in the art (Elble R. J. and Koller W. C. (1990): Tremor, John Hopkins University Press, Baltimore). The mean value can preferably be taken from this frequency range. Alternatively, instead of this, the frequency value to be expected on an age- and gender-specific basis can be used from a database.

For successful operation of the apparatus according to the invention, there is no need for the initially predetermined frequency to match the actually occurring frequency of the activity of the neuron population to be desynchronized. The control of the stimulation period T as described in 7.2.1 operates even when an initial value which differs to a major extent from the correct frequency value is used. In this case, differing to a major extent means that the value may even be too large or too small by a factor of at least 10. Alternatively, it is thus also preferably possible to start with a frequency value which is in the typical frequency range for the illness, as is known to those skilled in the art. The value of the frequency at the start of the stimulation can also preferably be obtained by individual matching to the respective patient. This may be done, for example, by means of a measurement of the neural activity prior to the stimulation, and estimation of the dominant frequency in the activity of the neuron population to be desynchronized, as described in Section 6.3b.

Choice of the frequency with previous operation of the apparatus: the mean value of the frequency during the previous operation of the apparatus is chosen as the start value for the frequency.

In both cases, that is to say with and without previous operation of the apparatus, the stimulation period T is calculated as the reciprocal of the start value of the frequency.

7.1.2 Time Delays

The time delays for the individual stimuli are preferably determined after initial definition of the stimulation frequency and of the stimulation period T. The time delays are preferably chosen as fractions of the stimulation period T, with a different time delay preferably being assigned to each individual stimulus. The time delays are preferably determined in such a way that the difference between the time delays corresponds to fractions of the stimulation period T, so that the difference between the time delays would thus be a multiple of T/N in the situation in which the time delays are equidistant. Equidistant time delays are, however, not necessary for successful desynchronization of the neuron population to be desynchronized. It is also preferable to choose time delays which correspond to a multiple of fractions of the stimulation period T and which may exceed the stimulation period T. The adaptation of the time delays as described in Section 7.2.2 also works in the situation described above, in which at least some of the time delays exceed the stimulation period T.

7.1.3 Intensity

The initial values of the stimulation parameters which determine the intensity of the individual stimuli (for example the gain of the feedback stimulation signal) are defined in accordance with the empirical values which are known to those skilled in the art (for example a maximum amplitude of 5 V). The intensity control as described in 7.2.3 works even when an initial value is used which differs to a major extent from the best intensity value. In this case, differing to a major extent means that the value may even be too large (maximum amplitude 5 V) or too small by a factor of at least 10. Alternatively, it is thus also preferable to start with an intensity value which is in the range that is known to those skilled in the art. In particular, it is preferable to start a stimulation with low values of the intensity, for example a maximum amplitude of 0.5 V, for the stimulation signals, in order in this way to reduce as far as possible the side-effects of the stimulation. If there is a need to use stronger stimulation signals, the intensity can be increased in small steps, as described in Section 7.2.3.

The initial values for the frequency and intensity can thus be predetermined, but in particular need not be predetermined in the course of a time-consuming calibration.

7.2 Adaptation of the Stimulation Parameters
7.2.1 Adaptation of the Stimulation Period T The neural activity is measured in the area to be desynchronized or in an area which is closely linked to it, and is used, after processing, as the stimulation signal. By way of example, in the case of Parkinson's disease, instead of a measurement by means of the sensors 3, a measurement of the activity in a subsequent area, for example the premotor cortex, by means of epicortical sensors, can also be carried out directly in the area to be desynchronized. The dominant mean period is determined in a time window with a length as stated in the following text. Various algorithms can be used for this purpose. For example, the instantaneous period can be determined as the time difference between two successive maxima of the measured neural activity. It is also, for example, possible to first of all estimate the mean frequency of the neural activity, and to define the stimulation period T as the reciprocal of the mean frequency. If not only illness-specific activity is measured by means of the sensor 3, the illness-specific activity must first of all be extracted, by bandpass filtering of the frequency range that is specific for that illness, for this type of frequency estimation. Alternatively, by way of example, the frequency can be determined by means of the frequency estimator that is mentioned in Section 6.3. The time window which is used for this frequency estimate has a length which may be open towards upper values and corresponds, for example, to 10 000 periods, preferably to 1000 periods and particularly preferably to 100 periods of the activity relating to the illness, or else to any other desired values.

7.2.2 Adaptation of the Time Delays

As described in Sections 3.3, 3.4 and 7.1.2, the time delays for the individual stimuli are typically chosen as fractions of the stimulation period T. By way of example, the time delays may be fixed during the stimulation, or may preferably be matched to the stimulation period that has been adapted in accordance with Section 7.2.1. In order to make it possible to achieve optimum desynchronization with a low stimulation intensity, the time delays of the individual stimuli are preferably varied during the stimulation by means of a deterministic or stochastic algorithm. For this purpose, the apparatus according to the invention has means in the form of the control unit 4 which allow the time delays of the individual stimuli to be varied during the stimulation. Furthermore, for example, the time delays can be varied not only within a stimulation period but also over a plurality of periods. In this case, the individual stimuli correspond to the processed neural activity which was measured at a time several periods earlier.

7.2.3 Adaptation of the Intensity

The sensor 3 is used to measure the neural activity which represents the activity of the neuron population to be desynchronized. This neural activity is passed to the unit 4 for signal processing and/or control purposes. The unit 4 for signal processing and/or control carries out a permanent, repetitive or demand-controlled stimulation in accordance with Section 6, with the intensity of the overall stimuli which are applied at the respective time being dependent on the extent of the pathological feature in the neural activity. The intensity can preferably be adapted for this purpose. The relationship between the stimulus intensity and the extent of the pathological feature can be controlled either manually or automatically as a function of the stimulation success. The extent of the pathological feature is determined in a time window with a freely variable, preferably constant, length, which ends at a constant time interval before the respective stimulus, in the following manner:

a) In the situation when the sensor 3 is used to measure exclusively or predominantly the pathological activity to be desynchronized and/or a neural or muscular activity which is closely linked to it, the amplitude of the extent of the synchronization corresponds to the neuron population to be desynchronized. The amplitude thus represents the pathological feature. The amplitude can in this case be estimated by determination of the maximum of the signal or by means of the mean value of the magnitude of the signal, or by bandpass filtering with subsequent Hilbert transformation or wavelet analysis. The first two variants (determination of the maximum of the signal or determination of the mean value of the magnitude of the signal) are particularly preferably used, since the calculation of the amplitude by means of a Hilbert transformation or wavelet analysis involves considerably more computation complexity, their accuracy depends on the correct choice of algorithmic parameters.

b) If the sensor 3 is used to measure not only the illness-specific activity but additionally inactivity which is not yet illness-specific, for example from other neuron populations, the neural activity cannot be used directly for estimation of the extent of the pathological feature. Since the illness-specific activity typically occurs in a frequency range which is not the same as the frequency range of the non-illness-specific activity, the activity in the illness-specific frequency range is preferably estimated in this situation. This is done, for example, by means of a frequency analysis. For example, the spectral energy can be determined in the illness-specific frequency range. As an alternative to this, the amplitude can be determined after bandpass filtering by determination of the maximum of the bandpass-filtered signal or by determination of the mean value of the magnitude of the signal, or by subsequent Hilbert transformation or wavelet analysis.

If the desired effect is not achieved, that is to say the target population is not desynchronized to an adequate extent and the pathological feature of the neural activity is therefore not shifted below the threshold value, the maximum intensity of the stimulus is slowly increased up to a maximum value, for example of 5 V, which is stringently predetermined for safety reasons (for example in steps of 0.5 V per 50 periods). For this purpose, the apparatus according to the invention has a controller which identifies any change in the neural activity and adapts the stimulating signals in the direction of higher values if there is no change in the neural activity. After about 20 successful periods of the stimulation, the apparatus can start to slowly reduce the maximum intensity of the stimulus (for example in steps of 0.5 V per 50 periods), provided that the stimulation is still successful. The stimulation success is determined during this process as described above. The controller is in this case programmed such that it identifies the change in the neural activity, and thus the stimulation success. The maximum stimulus intensity is preferably controlled on a time scale of between 10 and 1000 periods of the neural activity, such that the neuron population to be desynchronized is adequately desynchronized.

Independently of the value of the stimulation intensity as defined above, the amplitude of the stimulation signal is automatically minimized as a consequence of the characteristics, as described in Section 5, of the stimulation mechanism of the apparatus according to the invention after successful desynchronization.

7.3 Stimulation Parameters for the Situation in which at Least One Electrode 2 is not Located in the Neuron Population to be Desynchronized As in the situation described in Section 3.3 of an electrode 2 which is not located in the neuron population to be desynchronized, the neuron population to be desynchronized is influenced via an indirect stimulation, as described in Section 4.1.2. Since, in the case of indirect stimulation, the conduction times between the stimulated neuron populations on the one hand and the neuron population to be desynchronized on the other hand may each be of a different magnitude, the respective conduction times are first of all measured before carrying out the desynchronizing stimulation. Stimulation is for this purpose carried out via in each case one stimulation electrode 2, and the stimulus response is measured by means of the sensors 3 which are placed in the neuron population to be desynchronized. This is done separately n-times for all stimulation electrodes 2 which are used for indirect stimulation, with n typically being a small integer, up to for example 200. The mean conduction time is preferably estimated from this in the following manner:

The duration between the start of the stimulus application via the j-th electrode 2 and the first maximum in the stimulation response or in the magnitude of the stimulation response, $\tau_j^{(k)}$ is determined for each individual stimulus application. In the case of $\tau_j^{(k)}$, the index j represents the j-th electrode 2, while the index k represents the k-th applied stimulus.

The mean duration between the stimulus start and the stimulus response is then determined separately from this for each stimulation electrode 2 that is used for indirect stimulation, using the following formula 1:

$$\bar{\tau}_j = \frac{1}{L_j} \sum_{k=1}^{L_j} \tau_j^{(k)}. \qquad \text{Formula I}$$

In this case, $L_j$ is the number of stimuli applied via the j-th stimulation electrode 2. $L_j$ may but need not be the same for all stimulation electrodes 2 which are used for indirect stimulation.

The conduction time $\bar{\tau}_j$ determined in this way for the stimulation is taken into account in the following manner:

If a stimulus were applied by direct stimulation of the neuron population to be desynchronized with a time delay t of 2 via the j-th stimulation electrode 2, then, in the case of indirect stimulation, the stimulus would be administered with a time delay of t−$\bar{\tau}_j$ via the j-th stimulation electrode 2 for indirect stimulation, in which case t must be greater than $\bar{\tau}_j$, as can be done in accordance with Section 7.2.2.

The determination of the stimulation parameters at the start of the stimulation and the control mechanisms during the stimulation are completely analogous when the conduction times $\bar{\tau}_j$ are taken into account as described above, as described in Sections 7.1 and 7.2.

8 Advantages

The apparatus according to the invention has a number of advantages over existing apparatuses, for example DE 108 18 071.0-33 "Vorrichtung zur Desynchronisation von neuronaler Hirnaktivität" [Apparatus for desynchronization of neural brain activity]:

1. The major advantage of the apparatus according to the invention is that a physiological stimulus, specifically the feedback stimulation signal, that is to say the measured and processed neural activity of the neuron population to be desynchronized, is used for the stimulation. The self-regulating demand control of the stimulation amplitude as described in Section 5 thus takes place, thus minimizing the amount of energy introduced into the neuron population to be desynchronized, and thus lead to side-effects that are minor.
2. Because of the self-regulating stimulation amplitude in accordance with Section 5, the operation of the apparatus according to the invention saves power, since not only is a power-saving signal used for stimulation on the basis of the demand-controlled stimulation amplitude, but a saving in energy can also be expected in the case of the control apparatuses according to the invention, as are required for stimulation control. This makes it possible to achieve longer intervals between the necessity for battery changes, which is burdensome for the patient.
3. The embodiment of the repetitive or permanent application with demand-controlled stimulus intensity is particularly advantageous, since no threshold need be detected with this method. This embodiment can thus be implemented with considerably simpler algorithms. Its software and/or hardware implementation is accordingly considerably less complex.
4. In the case of permanent and repetitive stimulation with demand-controlled stimulus intensity and direct stimulation of the neuron population to be desynchronized, no calibration is required, that is to say there is no need to carry out a series of test stimuli in which the stimulation parameters are varied systematically, thus leading to the calibration duration being shorter.
5. The calibration which is carried out according to the invention is quicker, less susceptible to errors and is less complex since, in the case of direct stimulation, it is possible to start stimulation operation without any test stimulation, with the parameters being optimized in the course of stimulation operation, as described in Section 7.2. Because the calibration can be carried out quickly, the apparatus according to the invention can even be used intraoperatively, thus optimizing the placing of the deep electrodes 2. This makes it possible to use the effect of the desynchronizing stimulation on the extent of the symptoms, for example the tremor, directly as a parameter, for the quality of the placing.
6. The calibration according to the invention is less susceptible to errors since the frequency and conduction time estimators that are used in the course of the calibration according to the invention do not depend critically on parameters such as the limits and the characteristics of a bandpass filter. This embodiment can thus be implemented with considerably simpler algorithms. Its software and hardware implementation is accordingly considerably less complex.
7. Overall, one major advantage is the general tolerance and robustness of the apparatus according to the invention compared to the estimation of the parameters of intensity, stimulation period and time delays.
8. Because of the use of the possibly different stimulation effect as a function of the distance between the electrode and the area to be stimulated, and use of the pathologically increased coupling between the neurons in the neuron population to be desynchronized, the apparatus according to the invention stabilizes the area to be desynchronized in a desynchronized and desired state. This state is provided permanently and thus brings the area to be desynchronized very close to the physiological state. By way of example, long-lasting desynchronization is attained without any fluctuation backwards and forwards between resynchronization and a cluster state.

Example

If stimulation is carried out, for example, at four locations, then, by way of example, the following stimuli can be emitted via the four electrodes:

1. The feedback stimulation signal, that is to say the processed neural activity, is applied via each of the electrodes, with the stimulation signals in each case being offset by T/4 in time, as shown in FIG. 3, when T is the mean period of the rhythm of the neuron population to be desynchronized.
2. As is illustrated in FIG. 4, stimulation signals with the same time delay but of different polarity are applied via the electrodes 1 and 2. The same stimulation signals with a different polarity are likewise applied via the electrodes 3 and 4.

By way of example, the stimulation is carried out with three different control mechanisms, as described in Section 6, for the stimulus application thus preferably allowing demand-controlled and thus power-saving and mild (avoiding side-effects) stimulation, as described in Section 7:

1. Permanent stimulus application: the stimulation is carried out permanently, see FIG. 2, preferably with adaptation of the stimulation period. As can be seen by way of example in FIG. 2, desynchronization of the neuron population to be desynchronized occurs directly after application of the stimulation. This minimizes the amplitude of the measured neural activity, see FIG. 2b. At the same time, as can be seen by way of example in FIG. 2c, the stimulation amplitude is minimized because of the self-regulating demand control mechanism as described in Section 5. Once the stimulation has been switched off, resynchronization occurs after a short time, owing to the pathological interaction between the neurons in the population.
2. Demand-controlled stimulus application (that is to say demand-controlled choice of the start and end times of the stimulation) of the overall stimuli: if the synchronization of the nerve cell population exceeds a threshold value, the next overall stimulus is emitted via all of the electrodes, as described in Section 6.3.
3. Repetitive stimulus application: repetitive stimulation is carried out with coordinated stimuli via all of the electrodes. In this case, the intensity of the stimuli is matched to the intensity of the synchronization of the neuron population: the greater the synchronization, the stronger is the coordinated stimulus.

In this variant, $\tau/4$ can preferably be chosen rather than T/4 as the time delay between the individual stimuli, where T is the period of the rhythm without stimulation $\tau$ is the period forced on the rhythm by the stimulation. In other words: $1/\tau$ is the frequency of the stimulation signal with which the individual stimuli are applied. This results in the only critical stimulation parameter to which the system is subject: instead of determining this in a suitable form in the course of a complex calibration, it is dictated by the stimulation. Furthermore, this form of demand-controlled stimulation makes use of the fact that the neurons in the relevant regions have a tendency (because of the illness) to periodic firing or bursts (rhythmic production of groups of action potentials). It is therefore possible to achieve an entrainment of the neural activity of the neuron population to be desynchronized, with respect to the applied frequency.

In all three of the control methods described by way of example above, self-regulating demand control, as described in Section 5, results in the amount of energy introduced into the target population being minimized. In this case, it is preferably possible to adapt the only important stimulation parameters, the stimulation period T and thus the time delays, between the individual stimuli, by measurement of the frequency of the nerve cell population in the target region, or of another nerve cell population which is closely linked to it.

The lack of time-consuming calibration and stabilization of the effect even in the event of relatively major frequency fluctuations—particularly in the case of method 1 (permanent stimulation)—has important consequences:

1. The stimulation success can be checked immediately, intraoperatively, during the insertion of the deep electrode. This makes it possible to considerably improve the finding of the suitable target point. A calibration process which lasts for more than 30 minutes per electrode is required for the previous demand-controlled methods. This cannot be carried out intraoperatively and is not acceptable to the patient (who is not anesthetized).
2. The new stimulation methods can also be used for neurological and psychiatric illnesses in which pathological rhythms have highly fluctuating frequencies. In particular, the new methods can also be used to desynchronize rhythms which occur intermittently (that is to say which occur for a short time). This means that the new stimulation methods can be used for many more illnesses, and particularly even in the case of epilepsies.

The following illnesses and symptoms can be treated by means of the new stimulation method with the apparatus according to the invention by desynchronization of suitable brain areas.

In the case of all neurological and psychiatric illnesses in which pathological neural synchronization plays a relevant role for the extent of the illness-specific symptoms, for example: Parkinson's disease, essential tremor, dystonia, compulsion disorder, tremor in the case of multiple sclerosis, tremor as a consequence of a stroke or other tissue damage, for example tumorous tissue damage, for example in the area of the thalamus and/or the basal ganglia, choreoathetosis and epilepsy, although this list is not intended to be restrictive.

By way of example, the following target areas are used for the standard method of high-frequency continuous stimulation that is used at the moment:

In the case of Parkinson's disease the nucleus subthalamicus or in the case of tremor-dominant Parkinson's disease the thalamus, for example the nucleus ventralis intermedius thalami.

In the case of essential tremor the thalamus, for example the nucleus ventralis intermedius thalami.

In the case of dystonia and choreoathetosis the globus pallidum internum, in the case of epilepsy the nucleus subthalamicus, the cerebellum, thalamic core regions, for example the nucleus ventralis intermedius thalami, or the nucleus caudatus.

In the case of compulsion disorders, the capsula interna or the nucleus accumbens.

By way of example, the target areas listed above for the respective illnesses may be chosen for the apparatus according to the invention. Because either no calibration is required or the calibration can be carried out very quickly for the apparatus according to the invention, this makes it possible to test alternative target areas in the course of the electrode implantation process, for which the desynchronizing effect of the apparatus according to the invention may turn out to be even better.

The invention likewise covers a controller which controls the described method of operation of the apparatus according to the invention, as well as the use of the apparatus and of the controller for the treatment of illnesses including Parkinson's disease, essential tremor, dystonia, compulsion disorders, choreoathetosis, tremor in the case of multiple sclerosis, tremor as a consequence of a stroke or of some other tissue damage, for example tumorous tissue damage, for example in the area of the thalamus and/or the basal ganglia, and epilepsy.

The apparatus according to the invention can be used both as an implant for permanent therapy for the above-mentioned neurological and psychiatric illnesses and for intraoperative target point diagnosis, that is to say intraoperative finding of the optimum target point for the electrode implantation.

The invention claimed is:

1. An apparatus for desynchronization of neural brain activity, comprising:
    at least one sensor to measure a neural activity signal of a neuron population located in a brain to be desynchronized;
    a plurality of electrodes to stimulate the neuron population to be desynchronized; and
    a controller configured to process the measured neural activity signal and feed the processed neural activity signal into each of the plurality of electrodes as a stimulation signal to stimulate the neuron population in order to desynchronize the neuron population, the processing of the measured neural activity signal consisting of delaying the measured neural activity signal in time and one or more of filtering the measured neural signal, amplifying the measured neural activity signal, changing a polarity of the measured neural activity signal, and restricting the maximum amplitude of the measured neural activity signal.

2. The apparatus as claimed in claim 1, wherein the controller emits the stimulation signal to a first electrode and a second electrode of the plurality of electrodes with a first time delay and a second time delay, respectively, and the first time delay is different from the second time delay.

3. The apparatus as claimed in claim 2, wherein the controller emits the stimulation signal to a third electrode of the plurality of electrodes with a third time delay and the difference between the first and second time delays is essentially equal to the difference between the second and third time delays.

4. An apparatus for desynchronization of neural brain activity, comprising:
   at least one sensor to measure a time development of a neural activity signal of a neuron population located in a brain to be desynchronized;
   a plurality of electrodes to stimulate the neuron population to be desynchronized; and
   a controller configured to process the measured time development of the neural activity signal and feed the processed time development of the neural activity signal into each of the plurality of electrodes as a simulation signal to stimulate the neuron population in order to desynchronize the neuron population, the processing of the measured time development of the neural activity signal consisting of delaying the measured time development of the neural activity signal in time and one or more of filtering the measured time development of the neural activity signal, amplifying the measured time development of the neural activity signal, changing a polarity of the measured time development of the neural activity signal, restricting the maximum amplitude of the measured time development of the neural activity signal, linearly and/or non-linearly combining the measured time development of the neural activity signal and another measured time development of the neural activity measured by a sensor other than the at least one sensor, and coding the measured time development of the neural activity signal as a pulse sequence.

5. The apparatus as claimed in claim 4, wherein the controller emits the stimulation signal to a first electrode of the plurality of electrodes and the controller changes the polarity of the stimulation signal and emits the stimulation signal having its polarity changed to a second electrode of the plurality of electrodes.

6. A method for desynchronization of neural brain activity, comprising:
   measuring a time development of a neural activity signal of a neuron population located in a brain to be desynchronized; and
   processing the measured time development of the neural activity signal into a stimulation signal that is fed into each of a plurality of electrodes as a stimulation signal to stimulate the neuron population in order to desynchronize the neuron population, the processing consisting of delaying the measured time development of the neural activity signal in time and one or more of filtering the measured time development of the neural activity signal, amplifying the measured time development of the neural activity signal, changing a polarity of the measured time development of the neural activity signal, restricting the maximum amplitude of the measured time development of the neural activity signal, linearly and/or non-linearly combining the measured time development of the neural activity signal and another measured time development of the neural activity measured by a sensor other than the at least one sensor, and coding the measured time development of the neural activity signal as a pulse sequence.

7. The method as claimed in claim 6, wherein the stimulation signal is emitted to a first electrode and a second electrode of the plurality of electrodes with a first time delay and a second time delay, respectively, and the first time delay is different from the second time delay.

8. The method as claimed in claim 7, wherein the stimulation signal is emitted to a third electrode of the plurality of electrodes with a third time delay and the difference between the first and second time delays is essentially equal to the difference between the second and third time delays.

9. A method for desynchronization of neural brain activity, comprising:
   measuring a time development of a neural activity signal of a neuron population located in a brain to be desynchronized;
   processing the measured time development of the neural activity signal into a stimulation signal, the processing consisting of delaying the measured time development of the neural activity signal in time and one or more of filtering the measured time development of the neural activity signal, amplifying the measured time development of the neural activity signal, changing a polarity of the measured time development of the neural activity signal, restricting the maximum amplitude of the measured time development of the neural activity signal, linearly and/or non-linearly transforming the measured time development of the neural activity signal and another measured time development of the neural activity measured by a sensor other than the at least one sensor, and coding the measured time development of the neural activity signal as a pulse sequence; and
   feeding the stimulation signal into each of a plurality of electrodes to stimulate the neuron population in order to desynchronize the neuron population.

10. The method as claimed in claim 9, wherein the stimulation signal is emitted to a first electrode of the plurality of electrodes and the stimulation signal having its polarity changed is emitted to a second electrode of the plurality of electrodes.

* * * * *